United States Patent [19]

Paddock

[11] 4,362,867
[45] Dec. 7, 1982

[54] RECOMBINANT CDNA CONSTRUCTION METHOD AND HYBRID NUCLEOTIDES USEFUL IN CLONING

[75] Inventor: Gary V. Paddock, Mount Pleasant, S.C.

[73] Assignee: Research Corporation, New York, N.Y.

[21] Appl. No.: 214,648

[22] Filed: Dec. 10, 1980

[51] Int. Cl.$^3$ .................. C07H 15/12; C12P 21/00; C12P 21/02; C12P 19/34; C12P 15/00; C12N 1/00

[52] U.S. Cl. .................................. 536/27; 536/28; 435/68; 435/70; 435/91; 435/172; 435/317

[58] Field of Search .................. 435/91; 536/27, 28

[56] References Cited

PUBLICATIONS

Salser, in *Genetic Engineering*, Chakrabarty (ed.), CRC Press, West Palm Beach, Fla., pp. 53–81 (1978).
Kavsan et al., Chem. Abstr. 92, 224 123526h (1980).
Romano et al., Chem. Abstr. 91:170822r (1979).
Hartman et al., Chem. Abstr. 87:147246q (1977).
Waqar et al., Chem. Abstr. 84:100898b (1976).
Ogawa et al., Chem. Abstr. 87, 17513n (1977).

*Primary Examiner*—Alvin E. Tanenholtz
*Assistant Examiner*—James Martinell
*Attorney, Agent, or Firm*—Cooper, Dunham, Clark, Griffin & Moran

[57] ABSTRACT

Compounds useful as complementary DNA (cDNA) include deoxyribonucleotides and at least one ribonucleotide. They may be depicted by the general formula:

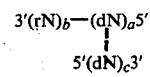

wherein $(dN)_a$ and $(dN)_c$ represent series of deoxyribonucleotides and $(rN)_b$ represents a series of ribonucleotides; wherein a, b, and c are the number of nucleotides in the series, with the proviso that b is $\geq 1$, a is $\geq 35$, and c is $\geq 10$; wherein the series of deoxyribonucleotides $(dN)_a$ includes a series of deoxyribonucleotides which is substantially complementary to the series of deoxyribonucleotides $(dN)_c$ and the dashed line represents noncovalent bonding between the complementary deoxyribonucleotide series; and wherein the solid line represents a covalent phosphodiester bond.

These compounds may be prepared from messenger RNA (mRNA) containing the genetic information necessary for cellular production of desired products such as polypeptides. After appropriate modification, they may be combined with DNA from a suitable cloning vehicle such as a plasmid and the resulting combined DNA used to transform bacterial cells. The transformed bacterial cells may then be grown and harvested; and the desired product or products recovered.

4 Claims, 1 Drawing Figure

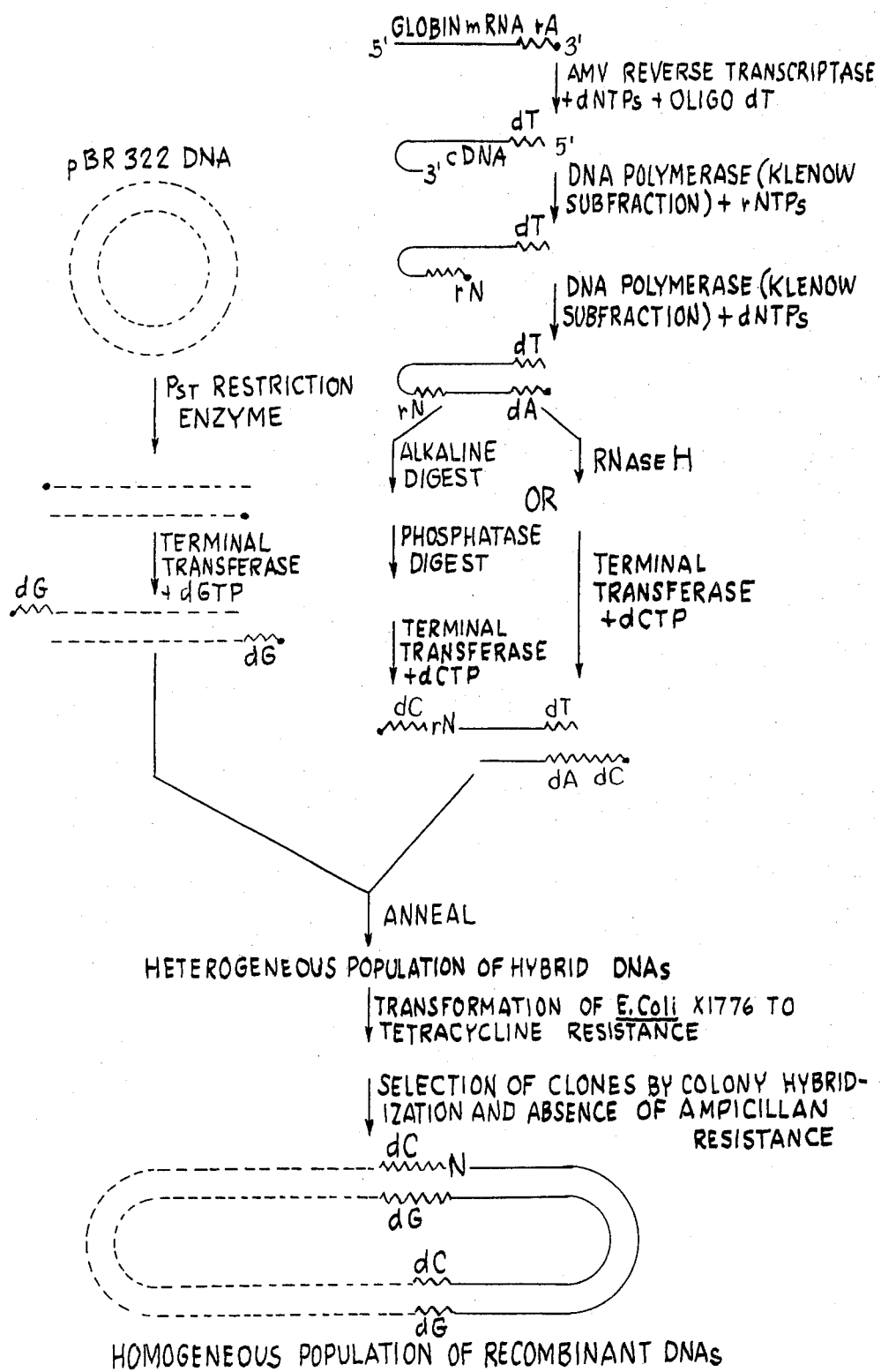

RECOMBINANT CDNA CONSTRUCTION METHOD AND HYBRID NUCLEOTIDES USEFUL IN CLONING

The invention described herein was made in the course of work partly supported by Grant Number GM-24783 from the National Institute of Health, Department of Health and Human Services.

FIELD OF THE INVENTION

This invention generally concerns the preparation of recombinant complementary DNAs (cDNAs) and cDNA analogs coding for cellular production of desirable products such as polypeptides. It also concerns novel compounds which include both deoxyribonucleotides and ribonucleotides. Finally, it concerns the use of such compounds in bacterial cloning.

BACKGROUND OF THE INVENTION

One of the major areas of research in molecular biology today concerns gene organization and expression in eukaryotic cells. Much effort has been spent on studies of RNA transcription and its subsequent processing to mRNA. It is currently thought that the genome sequences surrounding the cap site contain the signal for initiation of mRNA transcription or, alternatively, that very rapid processing cleaves away the first few nucleotides followed by capping at the 5' end. [Konkel, D. A., Tilghman, S. M., and Leder, P., (1978), Cell, 15: 1125-1132; Konkel, D. A., Maizel, J. V., Jr., and Leder, P., (1979), Cell, 18: 865-873; Gannon, F., O'Hare, K., Perrin. F., LePennec, J. P., Benoist, C., Cochet, M., Breathnach, R., Royal, A., Garapin, A., Cami, B., and Chambon, P., (1979), Nature, 278: 428-434; Nishioka, Y. and Leder, P., (1979), Cell, 18: 875-882; and Kinniburgh, A. J. and Ross, J., (1979), Cell, 17: 915-921. ] In either case, the nucleotide sequences contained in the 5' untranslated regions of mRNA, especially those near the cap site, are of prime importance to proper gene regulation, as illustrated by the extensive conservation of sequences found in this region for alpha and beta globin and other mRNA species. [Konkel, D. A., Tilghman, S. M., and Leder, P., (1978), Cell, 15: 1125-1132; Konkel, D. A., Maizel, J. V., Jr., and Leder, P., (1979), Cell, 18: 865-873; and Lockard, R. E. and RajBhandary, U. L., (1976), Cell, 9: 747-760.] In addition to transcription and processing of mRNA, these sequences undoubtedly play an important role in the translation of protein from mRNA. Indeed, the importance of the nucleotides contained in the 5' untranslated regions of mRNA is emphasized by the variety of methods designed to sequence them. [Lockard, R. E. and RajBhandary, U. L., (1976), Cell, 9: 747-760; Baralle, F. E., (1977), Cell 10: 549 -558; Baralle, F. E., (1977), Nature, 267: 279-281; Baralle, F. E., (1977), Cell, 12: 1085-1095; Legon, S., (1976). J. Mol. Biol., 106: 37-53; Chang, J. C., Temple, G. F., Poon, R., Neumann, K. H. and Kan Y. W., (1977)., Proc. Natl. Acad. Sci. U.S.A., 74: 5145-5149; and Chang, J. C., Poon, R., Neumann, K. H. and Kan, Y. W., (1978), Nucl. Acids. Res., 5: 3515-3522.] Yet none of these methods permits sequencing of the 5' end of an impure mRNA obtained in low yield as is the case for most mRNAs. Furthermore, none of the cloning techniques developed thus far, (Higuchi, R., Paddock, G. V., Wall, R., and Salser, W., (1976), Proc. Natl. Acad. Sci. U.S.A., 73: 3146-3150; Maniatis, T., Kee, S. G., Efstratiadis, A., and Kafatos, F. C., (1976), Cell, 8: 163-182; Rougeon, F., Kourilski, P., and Mach, B., (1975), Nucl. Acids Res. 2: 2365-2378; Efstratiadis, A., Kafatos, F. C., and Maniatis, T., (1977), Cell, 10: 571-585; Rabbits, T. H., (1976), Nature, 260: 221-225; Rougeon, F. and Mach, B., (1976), Proc. Natl. Acad. Sci. U.S.A., 73: 3418-3422; and Wood, K. O. and Lee, J. C., (1976), Nucl. Acids Res., 3: 1961-1971.] have been successful in preserving these important terminal sequences. In fact, the most popular of these techniques is destined to destroy these sequences in part, because it relies upon use of Sl nuclease. [Higuchi, R., Paddock, G. V., Wall, R., and Salser, W., (1976), Proc. Natl. Acad. Sci. U.S.A., 73: 3146-3150.]

In order to preserve these important 5'-end signals, efforts have been undertaken to develop methodology which avoids the need for Sl nuclease. [Frankis, R., Gaubatz, J., Lin, F. K., and Paddock, G. V., The Twelfth Miami Winter Symposium (ed. Whelan, W. J., and Schultz, J., Academic Press, New York), vol. 17, in press (1980); and Gaubatz, J. and Paddock, G. V., (1980), Fed. Proc., 39: 1782.] These efforts have resulted in the discovery of the floppy loop method described herein. This method employs a ribosubstitution step so that cleavage of the hairpin loop can be carried out by alkali or ribonuclease. It avoids destruction of nucleotide sequence information which is lost if the hairpin is opened in the conventional manner with Sl nuclease. Thus, by elimination of the Sl nuclease step, whole genes can be synthesized without loss of genetic information. Moreover, the Sl nuclease technique is known to introduce errors in the sequence [Richards, R. I., Shine, J., Ulbrich, A., Wells, J. R. E., and Goodman, H. M., (1979), Nucl. Acids Res. 7: 1137-1146] through a mechanism which the present invention avoids. Finally, although it has been demonstrated that hormones (insulin) and interferon can be cloned via recombinant cDNA, it may not be possible to clone some genes in their entireties with the Sl nuclease technique because the hairpin loop may be extremely large and may even include part of the structural gene (i.e., part of the mRNA coding for protein.)

SUMMARY OF THE INVENTION

This invention provides various compounds which include both deoxyribonucleotides and at least one ribonucleotide. Certain of these compounds are useful in the preparation of cDNA and cDNA analogs. Others are useful in bacterial cloning. This invention also provides processes for preparing such molecules and using them in the production of desirable products such as polypeptides.

Specifically, compounds useful in the preparation of cDNAs and cDNA analogs may be prepared. These compounds may be depicted by the formula:

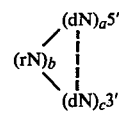   I wherein $(dN)_a$ and $(dN)_c$ represent series of deoxyribonucleotides and $(rN)_b$ represents a series of ribonucleotides; wherein a, b, and c are numbers of nucleotides in the series provided that b is $\geq 1$, a is $\geq 35$, and c is $\geq 10$; wherein the series of deoxyribonucleotides and $(dN)_a$ includes a series of deoxyribonucleotides which is substantially complementary to the series of deoxyribonucleotides $(dN)_c$ and the dashed line represents non-covalent bonding between the complementary deoxyribonucleotide series; and wherein the solid lines represent covalent phosphodiester bonds. Such compounds may be prepared as follows. A first molecule having the formula $3'(dN)_a5'$ is prepared. At least one ribonucleotide is added to the 3'-end of this molecule to produce a molecule having the formula $3'(rN)_b$—$(dN)_a5'$, and additional deoxyribonucleotides are then added to the 3'-end of the latter to produce the compounds.

If these compounds are treated with a reagent capable of breaking or disrupting either $5'(rN)$—$(dN)3'$ or $(rN)$—$(rN)$ bonds, or both, compounds useful as cDNA analogs or precursors may be prepared having the formula:

II wherein $(dN)_a$ and $(dN)_c$ represent series of deoxyribonucleotides and $(rN)_b$ represents a series of ribonucleotides; wherein a, b, and c are the numbers of nucleotides in the series; provided that b is $\geq 1$, a is $\geq 35$, and c is $\geq 10$; wherein the series of deoxyribonucleotides $(dN)_a$ includes a series of deoxyribonucleotides which is substantially complementary to the series of deoxyribonucleotides $(dN)_c$ and the dashed line represents non-covalent bonding between the complementary deoxyribonucleotide series; and wherein the solid line represents a covalent phosphodiester bond.

Further compounds having the formula:

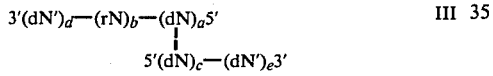

III may be prepared, wherein $(dN)_a$, $(dN)_c$, and $(rN)_b$ are as above and $(dN')_d$ and $(dN')_e$ represent series of identical deoxyribonucleotides; wherein a, b, and c are as above, and d and e are integral numbers of nucleotides in the series and are $\geq 10$; and wherein the solid lines represent covalent phosphodiester bonds. These compounds are prepared by adding deoxyribonucleotides dN' to the 3'-ends of compounds II.

Still other compounds may be prepared having the formula:

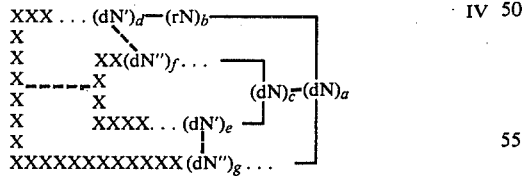

IV wherein $(dN)_a$ and $(dN)_c$ represent series of deoxyribonucleotides, $(dN')_d$, $(dN')_e$, $(dN'')_f$ and $(dN'')_g$ represent series of identical deoxyribonucleotides, the series $(dN')_d$ and $(dN')_e$ being complementary to the series $(dN'')_f$ and $(dN'')_g$ respectively, and $(rN)_b$ represents a series of ribonucleotides; wherein, a, b, c, d, e, f, and g are integral numbers of nucleotides in the series; provided that b is $\geq 1$, a is $\geq 35$, and c, d, e, f, and g are $\geq 10$; wherein the series of deoxyribonucleotides $(dN)_a$ includes a series of deoxyribonucleotides which is substantially complementary to the series of deoxyribonucleotides $(dN)_c$; wherein the xxx- lines represent double-stranded DNA derived from a cloning vehicle such as a plasmid, bacteriophage, or virus; wherein the dotted lines may be either no bond or covalent bonds; wherein the dashed lines represent non-covalent bonding between complementary deoxyribonucleotide series; and wherein the solid lines represent covalent phosphodiester bonds.

These molecules may be used to transform bacterial or eucaryotic cells, e.g., *Escherichia coli* cells, which may be grown in culture to produce desired products, including polypeptides.

BRIEF DESCRIPTION OF THE DRAWING

FIG. 1 is a schematic illustration of the ribosubstitution floppy loop recombinant cDNA technique showing alternative means for cleavage of the ribosubstituted hairpin double-stranded cDNA.

DETAILED DESCRIPTION OF THE INVENTION

Much publicity has been given to recent efforts to employ genetic engineering, particularly recombinant DNA technology, in the production of useful products such as insulin, interferon, growth hormone and the like. These attempts have often involved the insertion of a DNA molecule containing the genetic information necessary for cellular production of the desired product into host cells, especially bacterial cells. Bacterial cells into which such DNA molecules have been inserted can be grown in culture, resulting in the production of increased quantities of recoverable products.

One limitation upon such efforts is the availability of appropriate DNA molecules. Approaches which have been pursued to obtain these DNA molecules include synthesis of the molecules by conventional chemical methods and by reverse transcription of mRNA molecules which have been recovered from cells which contain DNA sequences coding for the desired product.

This invention is directed to improved methods of preparing these DNA molecules, called complementary DNA (cDNA). It is also directed to the preparation of novel hybrid molecules which include both deoxyribonucleotides and at least one ribonucleotide. Certain of these molecules are useful in the preparation of cDNA and cDNA analogs. Others are useful in bacterial cloning.

One such compound may be represented by the general formula:

I wherein $(dN)_a$ and $(dN)_c$ represent series of deoxyribonucleotides and $(rN)_b$ represents a series of ribonucleotides; wherein a, b, and c are the numbers of nucleotides in the series; wherein b is $\geq 1$, a is $\geq 35$, and c is $\geq 10$; wherein the series of deoxyribonucleotides $(dN)_a$ includes a series of deoxyribonucleotides which is substantially complementary to the series of deoxyribonucleotides $(dN)_c$ and the dashed line represents non-covalent bonding, particularly hydrogen bonding, between complementary deoxyribonucleotide series; and wherein the solid lines represent covalent phosphodiester bonds.

In such molecules the deoxyribonucleotide series $(dN)_a$ is an ordered polymer of deoxyribonucleotides which include the purines, adenine and guanine, and the pyrimidines, thymine and cytosine. The particular order of deoxyribonucleotides contains information necessary for cellular production of a desired product in accordance with the established genetic code, whereby groups of three nucleotides correspond to single amino acids which are assembled by cells into polypeptides. The precise order of the nucleotides may vary widely, depending upon the product for which the series codes. However, in the aforementioned compound I, the number of nucleotides, a, must generally be $\geq 35$ since fewer nucleotides do not permit sufficient formation of non-covalent bonding between complementary nucleotides in the series $(dN)_a$ and $(dN)_c$. More often, the number of nucleotides will be even greater, varying from as few as about 60 in the case of DNA sequences which code for oligopeptides, to about $10^3$ nucleotides for an average protein containing about 300 amino acids, and to $\geq 10^5$ for particularly large polypeptides.

The series $(dN)_c$ is also an ordered polymer, of at least 10 deoxyribonucleotides. The order of nucleotides is such that the nucleotide series $(dN)_c$ is complementary to an equal number of nucleotides in the series $(dN)_a$. In general, the length of the deoxyribonucleotide polymer $(dN)_c$ will be about 25 nucleotides shorter than the length of the series $(dN)_a$. The approximately 25 nucleotide difference may be attributed to nucleotides in the series $(dN)_a$ which are not base-paired with nucleotides in the series $(dN)_c$, but are involved in formation of a folded segment of nucleotides known to those skilled in the art as a hairpin structure. The minimum length of about ten nucleotides is necessary to permit sufficient non-covalent, hydrogen bonding between complementary nucleotides in the $(dN)_c$ and $(dN)_a$ polymer strands to form a double-stranded helical structure.

Situated between and covalently bonded to the series $(dN)_a$ and $(dN)_c$ is a series of ribonucleotides $(rN)_b$, wherein b is the integral number of nucleotides in the series and is $\geq 1$. It will be appreciated that, when $b=0$, the resulting molecule is a homopolymer of deoxyribonucleotides. Although b may vary considerably, it will generally be less than about 50 and oftentimes less than about 20. Moreover, in practicing the invention, it may be preferable to first form a molecule having the formula $3'(rN)_b—(dN)_a5'$, wherein b is $\geq 1$, then remove ribonucleotides until $b=1$, and finally add deoxyribonucleotides $(dN)_c$ to form molecules I, wherein $b=1$. In all molecules I, the ribonucleotide series $(rN)_b$ is covalently joined to the series $(dN)_a$ and $(dN)_c$ by means of $5' \rightarrow 3'$ and $3' \rightarrow 5'$ phosphodiester bonds, respectively.

Although the experiments described hereinafter involve globin polypeptides, it will be readily understood by those skilled in the art that the practices of this invention are widely applicable to polypeptides generally and to other desirable products. Thus, the deoxyribonucleotide series $(dN)_a$ may contain information in the form of its ordered nucleotide sequence for cellular production of any desired product, e.g., proinsulin, the polypeptide A chain of insulin, the polypeptide B chain of insulin, a growth hormone, an enzyme, a clotting factor, an antibody, or the polypeptide portion of one of the interferon glycoproteins. These examples are set forth to illustrate some of the better known commercial products which may be prepared in accordance with the present invention, but are not intended to be limiting, since countless other products may also be prepared.

In general, the deoxyribonucleotide series $(dN)_a$ will be obtained by reverse transcription of a messenger RNA (mRNA) molecule which itself will have been obtained by standard methods from a natural source, such as a eukaryotic cell known to contain a gene or genes coding for or otherwise associated with production of the desired product. However, it is also contemplated that the series $(dN)_a$ might be directly synthesized to create a polynucleotide having a sequence coding for a desired product.

Compounds I may be prepared as follows. Initially, a first molecule having the formula $3'(dN)_a5'$ is prepared either by conventional chemical synthesis, or preferably by reverse transcription of a mRNA molecule corresponding thereto. One method of accomplishing this result is to treat the mRNA molecule with a suitable enzyme, such as AMV reverse transcriptase, and a mixture of the deoxyribonucleotides, dATP, dCTP, dGTP, and dTTP, under appropriate conditions which permit formation of the $(dN)_a$ molecule. Suitable conditions are well known in the art and may include: a temperature of about 25°–45° C., e.g., 37° C.; a buffer having a pH of about 7.0 to 9.0, e.g., 8.3; a catalytic amount of enzyme; and a molar excess of the deoxyribonucleotide triphosphates.

In one embodiment of the invention, the mRNA molecule will include a series of repeating adenylate ribonucleotides at its 3'-end, the number of such being n, and formation of $(dN)_a$ involves addition of oligo dT, e.g., oligo $(dT)_{12-18}$, to the reaction mixture in sufficient quantity to permit formation of a $3'(dN)_a5'$ molecule having n repeating thymidylate deoxyribonucleotides at its 5'-end. In such molecules n is necessarily less than a.

Next, at least one ribonucleotide is added to the 3'-end of the $3'(dN)_a5'$ molecule to form a molecule having the formula $3'(rN)_b—(dN)_a5'$. Although ribonucleotide addition could be accomplished by conventional chemical methods, it is preferably effected by a ribosubstitution addition reaction utilizing a DNA polymerase, e.g., DNA polymerase I, and a mixture of the ribonucleotide triphosphates rATP, rGTP, rCTP, and rUTP under appropriate conditions to permit formation of the $3'(rN)_b—(dN)_a5'$ molecule. Once again, suitable conditions are known. They may include temperatures of about 25°–45° C., e.g., 37° C.; buffers having pH's of about 7.0, e.g., 7.4; molar excess of ribonucleotide triphosphates; and catalytic amounts of enzyme.

Finally, additional deoxyribonucleotides are added to the 3'-end of the $3'(rN)_b—(dN)_a5'$ molecule to form compound I. Here again, conventional chemical methods may be employed, or preferably enzymatic addition of the nucleotides may be utilized. In this regard, treatment of the $3'(rN)_b—(dN)_a5'$ molecule with a DNA polymerase, e.g., DNA polymerase I, and a mixture of dATP, dCTP, dGTP, and dTTP under suitable reaction conditions may be used. Suitable conditions may include temperatures from about 25°–45° C., e.g., 37° C.; buffers having pH's of about 7.0, e.g., 7.3; molar excess of nucleotide triphosphates; and catalytic amounts of polymerase.

The resulting compound I may then be recovered and purified by conventional techniques. Thereafter, it may be converted to a double-stranded molecule useful in bacterial cloning as described more fully hereinafter. Also, it may have uses in other areas, e.g., in pharmaceutical preparations or diagnostic tests.

If compound I is treated with a reagent capable either of breaking 5'(rN)—(dN)3' bonds alone or of breaking both 5'(rN)—(dN)3' and (rN)—(rN) bonds under suitable conditions (suitability being determined by the nature of the reagent and the precise identity of compound (I) a double-stranded compound can be prepared having the formula:

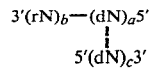   II wherein $(dN)_a$, $(dN)_c$, $(rN)_b$, a, b, c, and the dashed and solid lines are as indicated for compound I.

Suitable reagents include alkali, alkaline phosphatase, and RNase, particularly RNase H. The appropriate conditions for employing each such reagent vary in terms of temperature, time, pH, and the like. Generally, the reagents will be employed at temperatures in the range 25°–45° C., e.g., 37° C.; for reaction times from about 10 minutes to about 5 hours; and in buffers having pH's of about 7.0.

Compounds II can be converted to homogeneous cDNA by removal of all the ribonucleotides. The resulting compounds can be represented by formula II wherein $b=0$. Many such compounds are known. However, there may be some which are novel, particularly, in cases where the deoxyribonucleotide series $(dN)_a$ has been prepared by chemical synthesis and codes for an oligopeptide or polypeptide which does not occur in nature.

This invention contemplates the use of compounds II as cDNA analogs in subsequent cloning. In this application, it may be preferable to remove all ribonucleotides other than the first ribonucleotide joined to the $(dN)_a$ series of deoxyribonucleotides if this result has not already been effected by the reagent treatment.

Compounds II may be stored for subsequent use in bacterial cloning. Alternatively, the compounds may be distributed or sold for such use. Finally, the compounds may be employed immediately in cloning.

For cloning, it is generally desirable to add identical deoxyribonucleotides dN' to the 3'-ends of compounds II. This may be accomplished by known techniques, including treatment of compounds II with an enzyme, such as terminal transferase, and an excess of a single deoxyribonucleotide triphosphate dN'TP under suitable conditions. In this reaction N' may be any of G, C, T, or A.

This results in production of compounds which may be depicted by the formula:

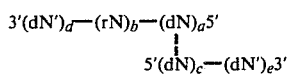   III wherein $(rN)_b$, $(dN)_a$, $(dN)_c$, a, b, c, and the dashed and solid lines are as indicated hereinabove; $(dN')_d$ and $(dN')_e$ represent series of identical deoxyribonucleotides; and wherein d and e are the number of nucleotides in the series, provided that d and e are $\geq 10$. It is generally necessary that d and e be $\geq 10$ in order for compounds III to be used in subsequent cloning. Also, d and e will generally not exceed about 20–40, although this is not a critical upper limit, only one of convenience. The precise number of nucleotides may be varied by varying reaction conditions, including molar equivalents of nucleotide triphosphates employed, as is true in the various similar reactions discussed herein.

Compounds III can be annealed with DNA molecules which have been derived from a cloning vehicle, such as a plasmid, opened if circular, and tailed at both 5'-ends with a series of deoxyribonucleotides dN" which is $\geq 10$ nucleotides in length. In order for annealing to occur dN" must be complementary to dN'. Annealing is carried out under suitable conditions known to the art and results in formation of compounds which may be depicted by the formula:

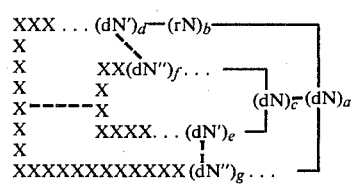   IV wherein $(dN)_a$ and $(dN)_c$ represent series of deoxyribonucleotides, $(dN')_d$, $(dN')_e$, $(dN'')_f$, and $(dN'')_g$ represent series of identical deoxyribonucleotides, the series $(dN')_d$ and $(dN')_e$ being complementary to the series $(dN'')_f$ and $(dN'')_g$ respectively; and $(rN)_b$ represents a series of ribonucleotides; wherein a, b, c, d, e, f, and g are the numbers of nucleotides in the series provided that b is $\geq 1$, a is $\geq 35$, and c, e, f, and g are $\geq 10$; wherein the series of deoxyribonucleotides $(dN)_a$ includes a series of deoxyribonucleotides which is substantially complementary to the series of deoxyribonucleotides $(dN)_c$; wherein the xxx-lines represent double-stranded DNA derived from a cloning vehicle; wherein the dotted lines may either be or not be covalent bonds; wherein the dashed lines represent non-covalent bonding between complementary deoxyribonucleotide series; and wherein the solid lines represent covalent phosphodiester bonds.

Generally, annealing alone will result in compounds IV wherein the dotted lines are not covalent bonds, but the presence of or subsequent treatment with a ligase or other suitable reagent can result in production of compounds wherein the dotted lines represent covalent bonds. Compounds IV, both open and closed-loop versions in which the dotted lines do and do not represent covalent bonds, are useful in cloning. Thus, for example, when the cloning vehicle-derived DNA is plasmid DNA, e.g., pBR322 DNA, and the $(dN)_a$ deoxyribonucleotide series includes the gene or genes coding for cellular production of a desired product or products, compounds IV can be used to transform bacterial cells, e.g., *E. coli* K-12 or $\chi1776$. The transformed cells which then contain compounds IV may be cloned, grown in culture, harvested, disrupted, and the desired product recovered. By appropriate construction of compounds IV to insure that the series $(dN)_a$ includes the information necessary for cellular production of the desired product, and to insure that the cloning vehicle DNA is appropriate for use in transforming the contemplated host cells, it should be possible to successfully produce numerous, commercially valuable products.

The following experiments are set forth to illustrate the practices of this invention, but should not be construed as limiting the invention which is defined by the claims which follow.

EXPERIMENTAL DETAILS
MATERIALS AND METHODS

Construction of recombinant cDNAs via the floppy loop technique was carried out as follows. Complementary DNA was synthesized in 0.1 ml to 0.4 ml 50 mM Tris-HCl, pH 8.3; 10 mM $MgCl_2$; 20 mM 2-mercaptoethanol; 30 µg/ml actinomycin D; 20 µg/ml oligo $(dT)_{12-18}$, obtained from Collaborative Research, Waltham, Mass.; 40–60 µg/ml rabbit globin mRNA; 1 mM each dATP, dGTP, dTTP, and dCTP [dCTP containing 50–250 µCi/µmol $^3H$ or $^{32}P$]; and 150 U/ml AMV reverse transcriptase, supplied by J. Beard through the Biological Carcinogenesis Branch, National Cancer Institute, NIH. Incubations in early experiments were carried out at 37° C. for 1 hr, but we have found incubation at 45° C. for 15–20 min to be far superior. The reaction mixture was then extracted with an equal volume of water-saturated phenol, and residual phenol was removed by extraction with an equal volume of ether. The cDNA was precipitated with 40 µg/ml yeast tRNA, 0.1 vol 3 M NaAc (pH 5.5) and 2.25 vol ethanol. The cDNA was resuspended in 0.2 ml $H_2O$, brought to 0.3 M in NaOH, and incubated at 90° C. for 30 min to hydrolyze the mRNA. The cDNA was then precipitated with 0.1 vol 3 M NaAc (pH 5.5), 0.1 vol 3 N HCl, 40 µg/ml yeast tRNA, and 2.5 vol ethanol. The cDNA was then chromatographed through a 0.6×15 cm column of Sephadex G-100 in 0.01 M triethylammonium bicarbonate, pH 8.5. The columns were prepared in silanized glass or plastic pipettes. One-ml tuberculin syringes have also been used, but in this case the oligo (dT) may not be removed. Yeast tRNA (40 µg) was chromatographed on a column prior to cDNA samples to fill nonspecific binding sites. The peak fractions were pooled and precipitated with 0.1 vol 3 M NaAc (pH 5.5), 40 µg/ml tRNA, and 2.25 vol EtOH.

The ribosubstitution step, modified from Whitcome, et al., [Whitcome, P., Fry, K. and Salser, W., (1974), Methods Enzymol. 29: 295–321], was carried out in 0.1 ml 67 mM Tris-HCl (pH 7.4), 0.67 mM $MnCl_2$; 1.0 mM 2-mercaptoethanol; 330 µM each rATP, rGTP, rUTP, and rCTP; 100 U/ml DNA polymerase I (Klenow large fragment from Boehringer-Mannheim); and 10–40 µg/ml cDNA for 10 min at 37° C. Recently, 5'-rAMP has also been added at 0.3 mM to prevent any possible degradation by the 3'-exonuclease activity contained in DNA polymerase I [Byrnes, J. J., Downey, K. M., Que, B. G., Lee, M. Y. W., Black, V. L. and So. A. G., (1977), Biochemistry 16: 3740–3746] during the slow ribosubstitution reaction. The cDNA reaction mixture was then extracted with water-saturated phenol and the residual phenol removed by ether extraction. Following the extraction, cDNA was chromatographed through Sephadex G-100, and the excluded material was precipitated with EtOH as above.

Second-strand synthesis was carried out as described by Higuchi, et al. [Higuchi, R., Paddock, G. V., Wall, R., and Salser, W., (1976), Proc. Natl. Acad. Sci. U.S.A. 73: 3146–3150.] The cDNA was resuspended in 0.12 ml 67 mM potassium phosphate, pH 7.3; 6.7 mM $MgCl_2$; 1 mM 2-mercaptoethanol; 33 µM each of dTTP, dCTP, dATP, and dGTP (dCTP containing 10 to 20 mCi/µmol $^3H$ or $^{32}P$) and incubated with 40 U/ml DNA polymerase I (Klenow large fragment) for 30 min at 37° C. The double-stranded hairpin cDNA reaction mixture was extracted with water-saturated phenol and ether, and precipitated with ethanol as above. The precipitate was resuspended in 0.1 ml $H_2O$, brought to 0.3 N in NaOH, and incubated at 90° C. for 30 min to hydrolyze the ribonucleotide link. The DNA was then precipitated with 0.1 vol 3 M NaAc, pH 5.5, 0.1 vol 3 N HCl, 40 µg/ml yeast tRNA, and 2.25 vol ethanol. The DNA was then resuspended in 0.1 ml 0.1 M Tris-HCl, pH 8.0, and treated with bacterial alkaline phosphatase (Worthington BAPF) as described by Shinagawa and Padmanabhan. [Shinagawa, M. and padmanabhan, R., (1979), Anal. Biochem. 95: 458–464.] The reaction mixture was supplemented with 0.1% SDS and incubated with 1.5–2.0 units of phosphatase which had been resuspended in 0.1 M Tris-HCl (pH 8), 10 µM $ZnSO_4$ for 1 hr at 37° C. [The removal of phosphate can be followed by including 1 µCi $^{32}P$-dNTP and at various times spotting 1 µl for cellulose thin-layer chromatography (methanol:HCl:$H_2O$, 7:2:1). The reaction mixture can be frozen until the degree of reaction is determined by autoradiography of the chromatograms.] The reaction mixture was then extracted four times with equal volumes of water-saturated phenol and one time with ether, and then chromatographed through Sephadex G-100, and the peak fractions were precipitated with ethanol as above.

The procedure for tailing the globin DNA with poly (dC) and Pst-cleaved pBR322 plasmid DNA with poly(dG) was modified from Chang, et al., [Chang, A. C. Y., Nunberg, J., Kaufman, R. J., Erlich, H. A., Schimke, R. T., and Cohen, S. N., (1978), Nature 275: 617–624,] using terminal transferase (prepaed in collaboration with M. S. Colemen at the University of Kentucky by the method of Chang and Bollum [Chang, L. M. S. and Bollum, F. J., (1971), J. Biol. Chem., 246: 909–916]) in 140 mM cacodylic acid, 30 mM Tris-base, 0.1 mM dithiothreitol, 1 mM $CoCl_2$, final pH 7.6, so that approximately 30 C residues were added to the globin DNA or 15–20 G residues to the pBR322 DNA. Incorporation was followed by acid precipitation of $^3$-dNTP. The DNAs were then subjected to extraction with an equal volume of water-saturated phenol and removal of residual phenol with ether. The pBR322 DNA was concentrated by precipitation with ethanol. The DNAs were then purified of precursors by chromatography through an 0.6×15 cm A5 m (Bio-Rad) column (previously treated with 40 µg yeast tRNA) in 0.1 M NaCl, 0.01 M Tris-HCl, pH 7.5. The peak fractions were then pooled and precipitated with ethanol as for the Sephadex G-100 columns above. More recently, Sephadex G-200 columns have been used for purification of the globin DNAs at this step in order to obtain better recovery of the DNA. Annealing of approximately equimolar amounts of globin and pBR322 DNA was carried out as described by Chang, et al., [Chang, A. C. Y., Nunbery, J., Kaufman, R. J., Erlich, H. A., Schimke, R. T., and Cohen, S. N., (1978), Nature, 275: 617–624] in 10 mM Tris-HCl, pH 7.5 0.25 mM EDTA, 0.1 M NaCl.

Transformation of E. Coli χ1776 to tetracycline resistance was performed by the method of Norgard, et al. [Norgard, M. V., Keem, K., and Monahan, J. J., (1978), Gene 3: 279–292.] Clones were then screened for absence of ampicillin resistance and for presence of globin gene sequences using the colony hybridization technique, [Grunstein, M. and Hogness, D. S., (1975), Proc. Natl. Acad. Sci. U.S.A. 72: 3691–3695] as modified by Sippel, et al. [Sippel, A. E., Land, H., Lindenmaier, W., Nguyen-Huu, M. C., Wurtz, T., Timmis, K. N., Giesecke, K., and Schutz, G., (1978), Nucl. Acids Res. 5: 3275-3294.]

Recombinant cDNAs were prepared for sequence analysis by cleavage with Bst NI (N. E. Biolabs) and labeled with $^{32}$P using T4 polynucleotide kinase (Boehringer-Mannheim) and [gamma-$^{32}$P] rATP (ICN). The labeled DNA was then cleaved with Pst I (N. E. Biolabs), and the fragments were separated by electrophoresis through a 6% polyacrylamide gel. The fragments containing the insert ends were easily determined by comparison with non-Pst I cleaved DNA loaded in an adjacent position.

Sequence analysis was performed by the method of Maxam and Gilbert [Maxam, A. M. and Gilbert, W., (1977), Proc. Natl. Acad. Sci. U.S.A. 74: 560-564] with the G-A reaction as described by Rogers, et al., [Rogers, J., Clarke, P. and Salser, W., (1979), Nucl. Acids Res. 6: 3305-3321], except that all reactions at 90° C. were performed under mineral oil in polypropylene tubes instead of in sealed glass capillaries.

RESULTS AND DISCUSSION

The floppy loop technique deviates from the S1 nuclease cDNA cloning method as follows (see FIG. 1): First, the 3' end of the cDNA acts as the primer for the addition of a short stretch o ribonucleotides by *E. coli* DNA polymerase I. Secondly, the ribonucleotide-terminated cDNA is used as a primer-template for synthesis of the second DNA strand by DNA polymerase, which is followed by treatment with alkali and phosphatase to open the hairpin loops and to regenerate a 3'-OH at this position, respectively. Obviously, treatment with alkali results in denaturation of double-stranded cDNA. Since the cDNA must be hybridized to the plasmid, however, reannealing of complementary sequences should take place without any additional steps. The resulting double-stranded DNA is then tailed with poly (dC) and annealed to the poly (dG)-tailed plasmid, pBR322, previously cleaved at the Pst site.

In preliminary experiments, several options were employed for incorporating the ribonucleotide desired for linking the first and second strands, because of uncertainty as to the best conditions for generating a reasonable length of ribonucleotides. In these experiments, ribonucleotides were added either by terminal transferase or by ribo-subsitution with DNA polymerase. All but one of the ribonucleotides were removed prior to second-strand synthesis by treatment with alkali, and the 3'-OH end was regenerated by treatment with phosphatase. The terminal transferase method has the advantage of marking the 5'-end with a known residue, but has the disadvantage that the nucleotide added may not base-pair with the first strand. It is known that the purpose of the 3'-exonuclease activity contained in the DNA polymerase is to remove mismatched nucleotides; thus, the ribonucleotide linker could be lost. This may be prevented, however, by adding a 5'-nucleotide monophosphate to the reaction mixture during second-strand synthesis. [Byrnes, J. J., Downey, K. M., Que, B. G., Lee, M. Y. W., Black, V. L., and So, A. G., (1977), Biochemistry 16: 3740-3746.] On the other hand, the ribosubstitution methods have the advantage of further stabilizing the cDNA 3' hairpin, but have the disadvantage of uncertainty with regard to the identity of the nucleotide at the cDNA 3' terminus, i.e., the nucleotide complementary to the 5'-mRNA terminal nucleotide, disregarding the inverted cap nucleotide, 7 meG. This is because it cannot be determined whether this nucleotide or the ribonucleotide added to it is the same (i.e., cytosine) as the poly (dC) tail added later. Of course, after plasmid replication in *E. coli*, the ribonucleotide will be converted to a deoxynucleotide. Thus, the following possibilities must always be considered when a sequence is eventually determined: (a) the real sequence is one nucleotide longer (i.e., both the 3'nucleotide and the ribonucleotide are cytosine); (b) the real sequence is as determined (i.e., the 3'nucleotide is not cytosine but the ribonucleotide is cytosine); or (c) the real sequence is one nucleotide shorter (i.e., neither the 3'necleotide nor the ribonucleotide is cytosine).

Of the various options tried, priming of the second-strand synthesis directly after synthesis of the linker was found to be much simpler, and the elimination of the extra steps required for removal of all but a single ribonucleotide resulted in smaller losses from handling. However, all of the various options for ribosubstitution were successful in yielding recombinant globin cDNA/pBR322 DNA molecules as determined by colony hybridization and antibiotic resistance. The efficiency of transformation obtained with these cDNAs was comparable to that obtained with the S1 method, which was performed concurrently. Of 48 clones analyzed, 30 had lost ampicillin resistance, indicating insertion of a rabbit globin cDNA segment into the original Pst site. Colony hybridization indicated that all 30 had globin gene inserts. Analysis of 27 of the recombinant plasmids revealed that Pst sites had been created at both ends of the insert in 21 recombinants (80%). The remainder had at least one of the possible Pst sites recreated.

The sizes for the inserted sequences in the 27 rabbit globin recombinants tests ranged up to 585 nucleotides, with most being 200 to 400 nucleotides including the poly(dC)-poly(dG) tails. A similar size range was observed for a duck globin floppy loop preparation, except that at least one recombinant contained an insert of approximately 800 nucleotides. Thus, most of the recombinants did not have inserted sequences representing the full length of the globin mRNA. It must be kept in mind, however, that the first goal was to develop the technique. In order to try a variety of approaches and options, cDNA was conserved by not subjecting it to a preparative sizing step in an acrylamide gel. Analysis of this particular cDNA preparation revealed that a good portion was less than full length. On the other hand, restriction enzyme analysis suggested, on the basis of the size of the inserts and comparison with cleavage sites expected for the rabbit globin genes [Efstratiadis, A., Kafatos, F. C. and Maniatis, T., (1977), Cell 10: 571-585; and Heindell, H. C. Lin, A., Paddock, G. V., Studnicka, G. M., and Salser, W. A., (1978), Cell 15: 43-44, ] that a few might contain the important 5'-end mRNA sequences. Thus far, it has been determined that the methodology does not introduce erroneous sequences, in that the first two rabbit globin recombinants sequenced match perfectly with the known sequence for rabbit beta globin [Efstratiadia, A., Kafatos, F. C., and Maniatis, T., (1977), Cell 10: 571-585.] This is an important consideration because the S1 nuclease technique has a known potential for introducing errors into the nucleotide sequence [Richards, R. I., Shine, J., Ulbrich, A., Wells, J. R. E., and Goodman, H. M., (1979), Nucl. Acids Res. 7: 1137-1146] through a mechanism that is avoided by the floppy loop technique. The floppy loop cDNA cloning method offers the promise of obtaining the 5' end sequences of mRNA and thus full length clones as well. The technique has been simplified to the point that second-strand synthesis directly after the ribosubstitution step would seem to be the method of choice. This also allows the use of alternatives to opening the loop with alkali. Recently, clones of duck globin cDNA recombinants were obtained where the loop was opened using RNase H as described more fully hereinafter. This approach eliminates the need to create a 3'-OH end with phosphatase, because a 3'-OH end results from cleavage with RNase H. In addition to simplicity, opening the loop by treatment with ribonuclease instead of alkali will probably prove to be more suitable for cloning of recombinant cDNAs representing minor mRNA species, because this eliminates the risk of denaturation and thus the need for subsequent reannealing. This denaturation, however, has not seemed to be a problem with the abundant globin mRNA sequences.

RNase H Cleavage of Ribosubstituted Hairpin Double-Stranded cDNA

Globin cDNA sequences have been cloned in which the floppy loop was opened by cleaving the ribonucleotide linker with *E. coli* RNase H instead of with alkali. This avoids the need for subsequent treatment with phosphatase.

The initial conditions found to be successful were the following:

| 22 ng DNA | | |
|---|---|---|
| 5 μl RNase H (0.2 units) | | |
| in[1]: | 50 mM | KCl |
| | 50 mM | Tris-HCl, pH 7.9 |
| | 10 mM | MgCl$_2$ |
| | 1 mM | 2-mercaptoethanol |
| | 50 μl | volume |
| Incubate for 1 hr at 37° C. | | |

[1]Buffer from Crouch, R.J., (1974), J. Biol. Chem., 249: 1314–1316.

The above conditions represent a vast overkill, since poly A tails have been removed from 15 μg of globin mRNA with only 0.4 units RNase H in 30 min. On the other hand, perhaps excess enzyme is required (although probably not this much) because once the first cleavage is made, the remaining ribonucleotides may not be continually base-paired for removal by RNase H since the hairpin loop may assume a variety of structures in equilibrium. For this reason, the incubation is done at 37° C. so that any structure that is assumed will have the same possibility for existence as when the ribonucleotide linker was synthesized. The buffer may also be changed to that used by Donis-Keller, H., [(1979), Nucl. Acids Res. 7: 179–192]. The removal of KCl will make the RNase H conditions closer to those used for ribosubstitution (although not identical). In addition, sharper bands have been obtained when this buffer was used for removal of globin mRNA poly A. The buffer from Donis-Keller as modified by Berkower, et al., [Berkower, I., Leis, J., and Hurwitz, J., (1973), J. Biol. Chem. 248. 5914–5921] includes:

| 40 mM | Tris HCl, pH 7.9 |
|---|---|
| 4 mM | MgCl$_2$ |
| 1 mM | dithiothreitol |
| 0.03 mg/ml | BSA (bovine serum albumin) |

The temperature will be kept at 37° C.

It is important that the RNase H be free of contaminating DNases. Three present commercial sources of RNase H are P-L Biochemicals, Bethesda Research Laboratories, and Enzo Biochem., Inc. However, it may be that these are tested for contaminating RNAses, not DNases. If so, any DNase present would have to be removed.

RNase H was purified from 50 gm *E. coli* MRE 600 (Grain Processing, Iowa). Cells were lysed as in Burgess and Jendrisak, [Burgess, R. R., and Jendrisak, J. J., (1975), Biochemistry 14: 4634–4638,] except that, after high speed shearing in the blender, the cells were also sonicated for 4' with 20 second pulses. The mixture was then spun at 24,000 rpm in a 45 Ti rotor. The conductivity of the supernatant was adjusted to that for 50 mM NH$_4$Cl; 20 mM Tris-HCl, pH 7.5; and 5% glycerol. The lysate was then loaded onto a phosphocellulose column equilibrated to 50 mM NH$_4$Cl, 20 mM Tris-HCl, pH 7.5, and 5% glycerol. After washing with this buffer (4 column volumes), RNase H was eluted with a 0.1 M–0.6 M NH$_4$Cl gradient (9 column volumes) as in Birenbaum, et al. [Birenbaum, M., Schlessinger, D., and Hashimoto, S., (1978), Biochemistry 17: 298–306.]

The P.C. peak fractions (contains both RNase III and RNase H) were loaded onto I.C. agarose for purification of RNase III (binds to column) as in Birenbaum et al., ibid. or Dunn. [Dunn, J. J., (1976), J. Biol. Chem. 251: 3807–3814.] The RNase H does not bind. The RNase H was concentrated in a dialysis bag covered with PEG and chromatographed through Bio-Rad A5M, as in Berkower et al. [Berkower, I., Leis, J., and Hurwitz, J., (1973), J. Biol. Chem. 248: 5914–5921] The peak RNase H fractions were again concentrated via dialysis in PEG and the RNase H was chromatographed in Sephedex G100. The peak RNase H fractions were dialyzed to Buffer D of Berkower et al., ibid., and chromatographed through DEAE Cellulose, also as in Berkower, et al. The peak fractions were pooled, concentrated by dialysis with PEG, and then dialyzed to storage buffer, again as in Berkower, et al. Note that the order of several columns has been inverted. Most of the RNase H did not bind to DEAE Cellulose and it is this wash-through product which has been used.

The RNase H was assayed for activity by digestion of $^3$H-polyl rA.poly dT at 37° C. and was found not to digest poly ($^3$H-rA.rU), duck 5S RNA, the heterogeneous sequences of duck globin mRNA, or cDNA.

What is claimed is:

1. A compound having the general formula:

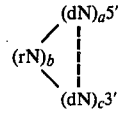

wherein (dN)$_a$ and (dN)$_c$ represent series of deoxyribonucleotides and (rN)$_b$ represents a series of ribonucleotides; wherein a, b, and c are the numbers of nucleotides in the series; with the proviso that b is $\geq 1$, a is $\geq 35$, and c is $\geq 10$, wherein the series of deoxyribonucleotides (dN)$_a$ includes a series of deoxyribonucleotides which is substantially complementary to the series of deoxyribonucleotides (dN)$_c$ and the dashed line represents a noncovalent bonding between complementary deoxyribonucleotide series; and wherein the solid lines represent covalent phosphodiester bonds.

2. A compound in accordance with claim 1 wherein the deoxyribonucleotide series $(dN)_a$ contains information necessary for cellular production of a desired product.

3. A compound in accordance with claim 2 wherein the series $(dN)_a$ contains the information necessary for cellular production of a polypeptide or a compound containing a polypeptide portion.

4. A compound in accordance with claim 3 wherein the polypeptide or compound containing a polypeptide includes proinsulin, the polypeptide A chain of insulin, the polypeptide B chain of insulin, a growth hormone, an enzyme, an antibody, or the polypeptide portion of interferon.

* * * * *